United States Patent [19]

Esty et al.

[11] 4,166,465

[45] Sep. 4, 1979

[54] ELECTROSURGICAL DISPERSIVE ELECTRODE

[75] Inventors: Janet M. Esty, Boulder; John A. Cox, Broomfield, both of Colo.

[73] Assignee: Neomed Incorporated, Boulder, Colo.

[21] Appl. No.: 842,463

[22] Filed: Oct. 17, 1977

[51] Int. Cl.² ................................................ A61N 3/06
[52] U.S. Cl. ........................... 128/303.13; 128/798; 339/253 R; 339/255 P
[58] Field of Search ............... 128/303.13, 404, 410, 128/411, 416–418, 413, 2.06 E, 2.1 E, DIG. 4; 339/253 R, 255 P, 260, 261

[56] References Cited

U.S. PATENT DOCUMENTS

| 1,005,283 | 10/1911 | Neher | 339/260 X |
|---|---|---|---|
| 1,662,446 | 3/1928 | Wappler | 128/416 |
| 2,110,392 | 3/1938 | Dorr | 128/413 |
| 3,547,105 | 12/1970 | Paine | 128/2.06 E |
| 3,566,860 | 3/1971 | Moe | 128/2.06 E |
| 3,568,662 | 3/1971 | Everett | 128/2.06 E |
| 3,606,881 | 9/1971 | Woodson | 128/2.06 E |
| 3,699,968 | 10/1972 | Bolduc | 128/303.13 |
| 3,720,209 | 3/1973 | Bolduc | 128/2.06 E |
| 3,805,769 | 4/1974 | Sessions | 128/2.06 E |
| 3,817,252 | 6/1974 | Maurer | 128/416 |
| 3,848,600 | 11/1974 | Patrick, Jr. et al. | 128/303.13 |
| 3,857,397 | 12/1974 | Brasseau | 128/411 X |
| 3,895,635 | 7/1975 | Justus | 128/303.13 |
| 3,911,906 | 10/1975 | Remhold, Jr. | 128/2.06 E |

FOREIGN PATENT DOCUMENTS

| 13888 | 10/1971 | Australia | 128/418 |
|---|---|---|---|
| 1181826 | 11/1964 | Fed. Rep. of Germany | 128/418 |
| 787477 | 9/1935 | France | 128/416 |
| 1241495 | 11/1959 | France | 339/253 R |
| 1288323 | 9/1972 | United Kingdom | 128/416 |

*Primary Examiner*—Lee S. Cohen
*Attorney, Agent, or Firm*—Reilly and Young

[57] ABSTRACT

A dispersive electrode has been devised for electromedical equipment consisting of a thin sheet or layer of electrically conductive material covered on one or both sides by a flexible laminate. To facilitate attachment to the skin of a patient during electrosurgery, the laminated sheet may be secured to a resilient backing member preferably having bifurcated ends to which an adhesive is applied in order to effect a secure connection to various parts of the body and to more readily conform to the contour of different parts of the body. The pad includes a tab projecting from one end of the conductive layer which tab is preferably of rounded or somewhat circular configuration and adapted to be inserted into a snap-type connector. The connector is in turn characterized by being a normally open connector having male and female, opposed snap-type fasteners which are pressed together through an opening in the tab into snap-fitting engagement with one another to provide a firm but flexible means of electrical connection into the plate during an electrosurgical operation. In the alternative, the tab may project rearwardly through a slot in the ground pad for connection to the electrical connector either by conventional connectors or a snap-type connector as described.

22 Claims, 5 Drawing Figures

U.S. Patent  Sep. 4, 1979  4,166,465
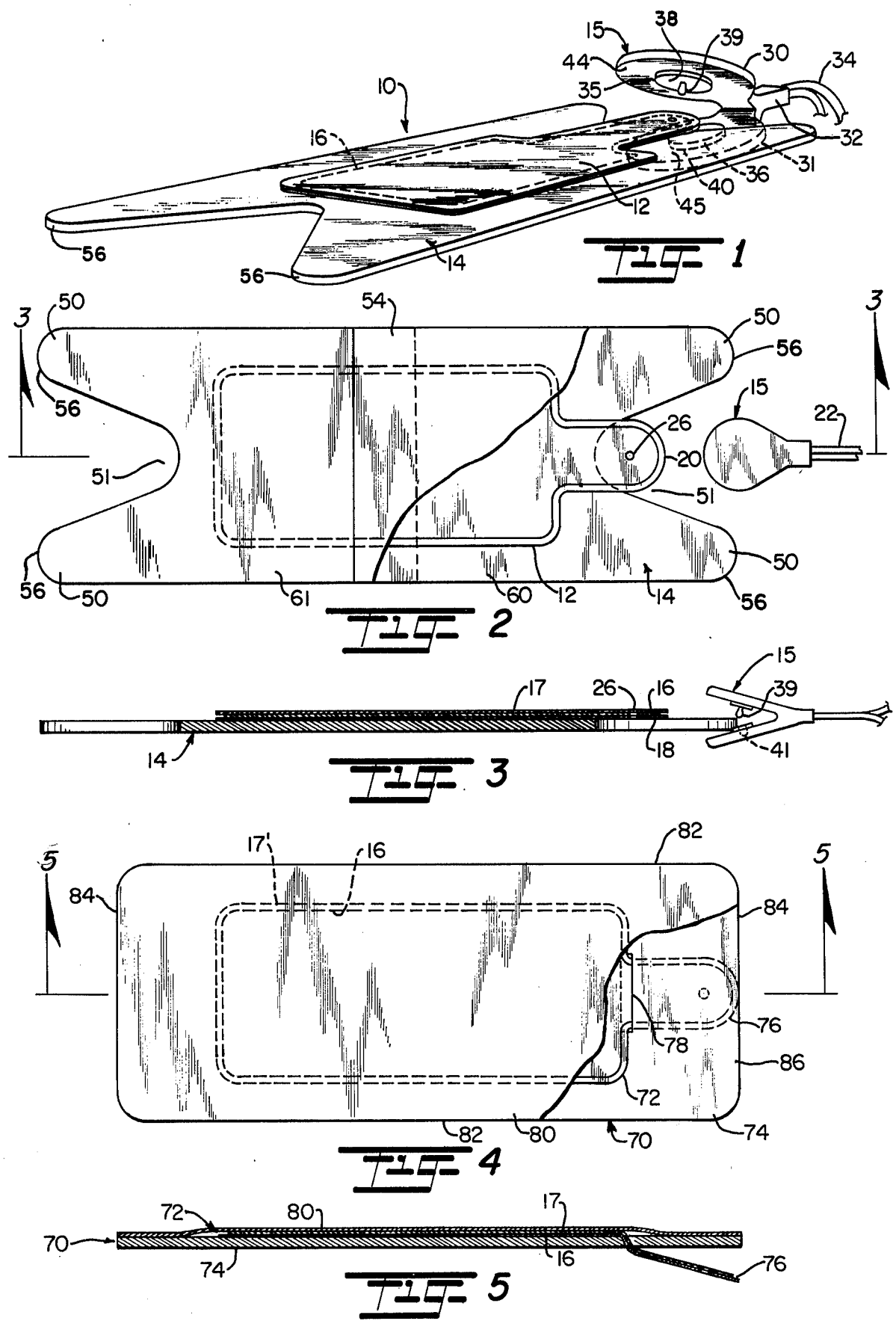

ELECTROSURGICAL DISPERSIVE ELECTRODE

This invention relates to dispersive electrodes and more particularly relates to a novel and improved electrosurgical dispersive electrode which is specifically adaptable for use in various electrosurgical procedures in which high frequency electrical current is employed.

BACKGROUND OF THE INVENTION

Various types of electrosurgical ground pads or dispersive electrodes have been devised to the end of affording a means of grounding the patient or dispersing current flow coming from the patient during an electrosurgical operation. Such ground pads have assumed different configurations according to the particular location of the body to which they are to be secured. Some of the first ground pads electrodes developed merely consisted of a flat metal plate having a connecting portion at one edge to facilitate interconnection of an electroconnector to the electrosurgical generator. It has also been proposed to employ thin metal plates or foil materials secured to a cardboard backing member. Other foil-type ground pads were devised in which a gel material was placed over the foil in order to effect a better electrical connection to the body while minimizing the risk of localized burning or hot spots often encountered with thin metal sheet or foil materials on account of their tendency to wrinkle.

Gels have become increasingly popular for use in connection with metal foil and are provided either separately or individually packaged so that the gel can be applied to the foil immediately prior to application of the pad to the body; or pre-gel ground pads electrodes are provided in which the pre-gel compound is encapsulated within an opening in the ground pad in direct electrical connection with the foil or other collector plate members. Generally, in the pre-gel types of ground pads electrodes, a connector may assume the form of a snap-type fastener electrically connected to the back of the collector plate to which may be affixed a lock-type of connector arrangement such as illustrated in U.S. Pat. No. 3,606,881 to Woodson; No. 3,895,635 to Justus, and No. 3,805,769 to Sessions.

The foregoing and other patents disclose the use of releasable connectors which can be attached to one end of the collector plate or to a tab projecting from one end of the plate. Generally, these connectors have demonstrated certain limitations either in failure to establish a positive connection, are subject to a certain amount of slippage or accidental loosening, or are limited in their freedom of movement once attached.

Electrodes which have been in most widespread use in electrosurgery are a conducting silver-silver chloride electrode which establishes a low impedance contact with the skin through a gel electrolyte. However, such conductive electrodes exhibit inadequacies which limit their effectiveness. For instance, the gels have a tendency to dry resulting in a significant increase in skin-to-electrode resistance which may produce unacceptably high current density levels. Bacterial and fungal growth can also take place in the gels, or a skin irritation often occurs when the electrolyte remains in contact with the skin for long periods of time. Wrinkling and flexing of these electrodes may increase the current density during an electrosurgical operation so that extreme tissue heating or RF burns may occur at the electrode site.

Accordingly, other so-called "dry" electrodes have been devised in addition to the more conventional metal plate or foil-type substrate, such as, for instance, the use of fine non-metallic electrically conductive particles which are applied directly by a solvent reactivated adhesive to the skin (Reinhold, Jr. U.S. Pat. No. 3,911,906 and Paine U.S. Pat. No. 3,547,105). The patent to Moe U.S. Pat. No. 3,566,860 discloses the use of a carbon-impregnated plastic in an adhesive coated web and also suggests utilization of a carbon or graphite with polytetrafluoroethylene while the patent to Woodson U.S. Pat. No. 3,606,881 is directed to the use of a pressure sensitive adhesive in combination with an electrode of silicon rubber with carbon, graphite or silver incorporated therein. U.S. Pat. No. 3,720,209 to Bolduc discloses a plate electrode of the type basically comprised of a one-piece flexible non-conductive sheet having a skin contacting electrically conductive layer with a clamp or jack-type electrical connector at one end. The patent to Maurer U.S. Pat. No. 3,817,252 teaches the use of conductive screens or foils in an EKG electrode.

SUMMARY OF THE INVENTION

Accordingly, it is an object of the present invention to provide for a novel and improved dispersive electrode for electro-medical use which is reliable and simplified in construction while avoiding a number of problems associated with prior electrodes.

Another object of the present invention is to provide a dry dispersive electrode which obviates the use of a gel and facilitates secure attachment to various parts of the patient's body; and further wherein the electrode may be incorporated into a flexible dispersive electrode which is readily conformable to different contours of the body.

A further object of the present invention is to provide a dispersive electrode which avoids wrinkling, and patient burns in use as well as to maintain safe current density levels.

A still further object of the present invention is to provide an electrosurgical dispersion electrode and electrical connector therefor in which the connector establishes a positive but flexible connection to the collector plate of the dispersive electrode in a new and useful manner.

In accordance with the present invention it is desirable to provide a collector plate which is preferably composed of a thin metal sheet or conductive layer having good electrically conductive properties and also is readily flexible. Thus the layer may be composed of aluminum, steel, steel alloys or conductive fibers. In association with the plate or conductive layer, a dielectric film is laminated over the conductive layer to form the interface between the conductive layer and the patient, but preferably is laminated to opposite sides of the conductive layer with the outer peripheral edges extending beyond the conductive layer and sandwiched directly together to encapsulate the metal plate or layer therein. As such, the laminated collector plate defines a capacitive coupling which has been found to be extremely excellent for transmission of RF energy in electrosurgical operations.

Both the area of the metal and thickness of the plastic laminate may vary according to the frequency range desired and the resultant laminate may be applied to a relatively thin flexible backing pad by suitable bonding means such as a high strength adhesive. Most desirably an outer edge of the backing pad extends beyond the metal plate to present an exposed surface in surrounding relation to the laminate for application of an adhesive. In the process of packaging, a thin paper covering or release paper may be applied over the adhesive edge of the backing pad and collector. The pad itself can be composed of any conventional type of insulating material which will act also as a flexible backing; however, it will be recognized that the opposite side of the laminate or coating to that applied to the skin may serve as a backing. Another feature of the backing pad is that it is notched to form bifurcated ends or wing portions which can be flexed and individually secured to the body of the patient so that the entire pad assembly will more readily conform to different parts of the body when applied thereto.

An additional advantage realized by employing bifurcated ends in the backing pads is to provide a recessed, protected portion for extension of the tab of the collector plate so as to facilitate a flexible but firm interconnection of the electrical connector end of the grond leads. Typically, there are a pair of return leads each leading into opposite sides of the connector which in the present invention is of the type composed of an insulated body in the general configuration of a clam shell, or rounded mating halves, flexibly interconnected in such a way as to be normally biased to an open position. Opposed confronting surfaces of the halves are provided with male and female snap-lock connectors, respectively, which are aligned with one another and adapted for insertion of the male connector through an opening provided in the tab extension of the collector plate into snap-fit connection with the female or socket portion. The cooperative disposition and relation between the connector and tab is such that the resultant connection is not only extremely flexible but will permit swivelling or rotation of the connector with respect to the tab and rest of the assembly.

An additional feature of the present invention is that the flexibility of the pad is such that it can be wrapped around itself which has not been generally true of commercially available pads. Generally, the plate size is selected to provide approximately one square centimeter per one and one-half watts of power delivered. Moreover, the thickness of the dielectric film is determined by the dielectric constant of the film material along with the voltage and frequency level for a given area of the collector plate in order to maintain a safe current density.

BRIEF DESCRIPTION OF THE DRAWINGS

Other objects, advantages and capabilities of the present invention will become more readily appreciated when taken in conjunction with the following detailed description of the preferred and modified forms of the invention and the accompanying drawings, in which:

FIG. 1 is a perspective view of a preferred form of an electrosurgical ground pad and releasable connector assembly.

FIG. 2 is a top plan view of a preferred form of assembly shown in FIG. 1.

FIG. 3 is a cross-sectional view taken about lines 3—3 of FIG. 2.

FIG. 4 is a top plan view with portions broken away of a modified form of ground pad in accordance with the present invention; and FIG. 5 is a cross-sectional view taken about lines 5—5 of FIG. 4.

DETAILED DESCRIPTION OF THE PREFERRED EMBODIMENT

Referring in more detail to the drawings, a preferred form of electrosurgical ground pad 10 is illustrated in FIGS. 1 to 3 and is broadly comprised of a dispersive electrode or insulated capacitive coupling member 12, flexible backing 14 and releasable connector 15. The capacitive coupling member 12 includes an electrically conductive layer or collector plate 16 encapsulated within outer flexible laminations 17 and 18, the outer or exposed lamination 17 defining a dielectric film to serve as an interface between the electrically conductive layer 16 and skin surface of the patient. A tab or extension 20 projects from one end of the electrode 12 and is exposed in a manner to be described to facilitate fastening of the electrical connector 15. The connector 15 is disposed at the terminal end of a cable 22 which is adapted for connection to suitable electrosurgical equipment, such as, an electrosurgical generator, not shown.

Considering in more detail the construction and arrangement of the dispersive electrode 12, the layer 16 is preferably fabricated from a thin metal sheet of generally rectangular configuration, the metal sheet being comprised of a material such as copper, aluminum, tin, stainless steel, brass, etc., or other highly conductive material with sufficient flexibility to conform to various contours of a patient's body. In the alternative, the collector plate 16 also may be made of electrically conductive particles, such as graphite, adhered to a flexible sheet, or may be made up of a layer of conductive fibers such as carbon impregnated fibers arranged on closely-spaced parallel relation to one another.

An important feature of the present invention relies in the encapsulation of the collector plate as described within flexible laminations 17 and 18. Here the laminations 17 and 18 are preferably composed of thin layers of a dielectric material which is capable of, and dimensioned to, encapsulate or seal the collector plate 16 therebetween so as to leave no exposed metal edges. Specifically, the outer lamination 17 serves as a dielectric film at the interface between the collector plates 16 and the patient's skin. Thus, the laminations may be composed of innumerable materials or combinations of materials, such as, those employed in fabricating credit cards and having a predetermined dielectric constant preferably in the range of 2 to 3.5, and which can be adhered to one another and to the backing member 14 so as to encapsulate the collector plate therebetween. Typical materials are cellulose acetate, the polyesters, polyethylene, silicone plastics, polyvinylchloride, and the polystyrenes. These materials not only have excellent dielectric properties but lend themselves well to application in sheet form such as by extrusion over the conductive layer 16 and can be heat-sealed or otherwise firmly bonded together to form a unitary electrode member with the desired flexibility to enable the entire electrode and pad to be readily flexed or bent to conform to the contour of various parts of a person's body. In this relation, it will be noted that the unitary electrode member includes not only the broader rectangular area of the collector plate, inner and outer plastic laminations as described but also forms the tab or extension 15 as well.

In accordance with well-known principles, capacitance for a parallel plate capacitor is calculated using the formula:

$$C = \frac{kA}{4\pi S}$$

where k is the dielectric constant of the material, A is the area of the collector plate 16 and S is the distance between the capacitor plates. In electrosurgery, the uniform current density is governed by the flow of electrons over the entire surface of one of the conductor plates and in effect the simultaneous "spill-over" flow of these electrons through the dielectric to the other conductor plate or skin. A dispersive electrode which is capable of uniformly distributing current flow greatly aids in preventing accidental electrosurgical burns which can occur if the current flows through small areas, or in other words resulting in a current density which exceeds the maximum permissible or safe level for the patient. Thus, accidental burns can occur as a result of slight irregularities in the contacting conductive surface causing hot spots which can result in painful and dangerous burns. It is therefore important that the electrode be so designed as to assure uniform application to the skin while establishing a uniform current density which will never exceed safe levels in normal operating situations.

In accordance with the present invention, the dry dispersive electrodes as described represent one conductive surface together with the separating dielectric cells for a parallel plate capacitor and the patient's body represents the second conductive surface of the capacitor. In electrical terms, current density can be established by the following formula:

$$\text{Current density } \left(\frac{I}{A}\right) = \frac{V \times f \times K}{2S}$$

It will be recognized from the above that for a given voltage (V) and frequency level (f) applied over a given surface area (A) of the electrode, the dielectric thickness (S) can be readily determined once the dielectric constant (K) of the material and the area (A) of the collector plate are known. Most desirably however the dielectric film is selected from materials which possess the characteristics of being flexible and capable of application in relatively thin layers over the conductive layer or plate 16 so as to encapsulate the plate therein and to assure uniform skin contact.

From the foregoing, for an electrosurgical generator in which the voltage range is 0 to 10 kV and the frequency is in the range of 100 KHz to MHz, a general purpose dispersive electrode was prepared in accordance with the present invention employing a collector plate composed of an aluminum foil material 2 mil thick which was laminated on both sides with a dielectric film composed of a polyester material having a thickness of 1 mil. Again, the thickness of the film layer on the side of the foil which would be in facing relation to the patient's skin is determined in accordance with the surface area of the foil and the dielectric constant of the film. Here, the dielectric constant of the film material is 3 and the area of the aluminum foil was 18 sq. in. The electrode is then applied by bonding to a surface of the insulated backing member or pad 14 where the pad is composed of a closed cell polyethylene film to which adhesive is applied across the entire surface, for application of the electrode, followed by application of a cover sheet or release paper as described to protect the surface when not in use, and finally for application to the patient.

As hereinbefore described, the connector 15 forms a continuation at one end both of the plate 16 and the laminations 17 and 18, and the tab is provided with an opening 26 sized to facilitate attachment of the electrical connector 15 while permitting metal-to-metal contact between the fasteners and plate. The electrical connector 15 is broadly comprised of corresponding connector halves 30 and 31 which are joined together along a limited portion of their outer peripheral surfaces to a common body 32. The body 32 is of generally rectangular configuration and is made hollow for insertion of the cable or electrical connector leads 34, one lead extending through a connector half 30 for electrical connection to a male contact 35 and another lead extending through the lower half 31 for direct connection to a female contact 36. The male and female contacts are preferably defined by complementary snap-fitting fastener positions as illustrated, the male portion 35 having a flat metal plate 38 provided with a downwardly projecting protuberance or button 39 slightly enlarged at its terminal end; and in turn the female portion having a flat metal plate 40 with a central socket or recess 41 of limited depth defined by spring-loaded surrounding wall portions adapted for snap-fitting insertion of the button 39 when the connector halves are forced together. In the preferred form, the connector halves 30 are of generally circular configuration and provide opposed confronting surfaces 44 and 45 to which the male and female contacts 35 and 36 are connected in aligned facing relation to one another. The entire connector 15 is preferably composed of a rubber or rubber-like material such as a thermoplastic having good insulating properties and possessed of some resiliency so that in formation the connector halves will normally be biased to an open position, as best seen from FIG. 3, with the male and female contacts spaced apart or separated from one another. However, when the connector halves are aligned with the tab 20 and specifically with the male and female contacts aligned with respect to the opening 26, the connector halves may be pressed inwardly to effect insertion of the male contact 39 through opening 26 and into the mating socket 41 of the female contact.

It will be appreciated that the coupling member 12 may be employed in direct combination with the electrical connector 15 and applied to the skin to serve as a dispersive electrode member without the aid of a separate backing member such as the backing member 14. However, in the preferred form, the backing member 14 is employed in combination with the coupling member 12 to facilitate its attachment to various parts of the anatomy and specifically in such a manner as to assure uniform surface contact. For this purpose, the backing member is preferably an elongated pad composed of a foam plastic having limited elasticity or stretchability. The pad is dimensioned to be of a generally rectangular size greater than that of the coupling and is provided with bifurcated ends or wings 50 which form a generally V-shaped, broad notch or recessed portion 51 between each of the bifurcated ends. The resultant configuration of the pad is thus somewhat of a butterfly configuration with the central notched area 51 permitting extension of the tab 20 from the coupling into the notched area in order to provide a clearance for attachment of the electrical connector between the surrounding edges or ends 50. Moreover, the bifurcated ends permit the entire assembly to more closely follow the contour of different parts of the body and for example the bifurcated ends define wrap-around end flaps which will allow secure attachment of the assembly at different application sites.

Preferably the coupling member 12 has its inner lamination 17 permanently bonded to the surface of the pad 14 leaving outer exposed or surrounding surfaces of the pad to which an adhesive is applied as generally designated at 54. Again, in the preferred form the backing member is preferably composed of a relatively porous foam material and the adhesive material employed may be selected from any of the well-known pressure sensitive adhesives which will not irritate the skin. The configuration of the bifurcated ends 50 preferably is such that the ends taper outwardly or away from the central body of the pad so as to terminate in rounded terminal edges 56, although it will be readily appreciated that the bifurcated ends may assume various different configurations and for instance may be provided either at one or both ends of the pad. As illustrated in FIG. 2, conventional peel-off type cover sheets or release paper 60 and 61 are applied over the adhesive coatings on the pad so as to protect the entire electrode when in storage or not in use.

DETAILED DESCRIPTION OF THE MODIFIED EMBODIMENT

A modified form of the present invention is illustrated in FIGS. 4 and 5 wherein a ground pad 70 is comprised of a capacitive coupling member 72 and backing member 74 with an extension tab 76 on the capacitive coupling 72 projecting rearwardly through a slot 78 in the backing member to permit attachment of an electrical connector, such as, the electrical connector 15 to the tab on the side of the backing member opposite to the capacitive coupling. In addition, a conventional cover sheet 80 is applied over the exposed surfaces both of the backing member 74 and capacitive coupling 72.

In the modified form, the composition of materials of the various components of the assembly correspond to those described with respect to the preferred form of invention as illustrated in FIGS. 1 to 3. However, the capacitive coupling member 72 is made up of a conductive layer 16 corresponding to the conductive layer 16 of the preferred form and a single outer lamination 17 which is superimposed onto the conductive layer and, while corresponding in configuration to that of the conductive layer and tab 76, is slightly enlarged with respect to the conductive layer and tab so as to provide an exposed or outer surrounding edge 17' for direct attachment such as by bonding to the front surface of the backing member, except for that portion surrounding the tab 76 which projects rearwardly with the tab through the slotted portion 78.

Again the composition of the pad itself corresponds to the composition of the pad or backing member 14 but in the modified form is of elongated rectangular configuration so as to provide opposite parallel sides 82 and opposite parallel ends 84. The backing member or pad is dimensioned to be of a greater area than that of the coupling member 72 so as to provide exposed surrounding surfaces to which a pressure-sensitive adhesive 86 is applied for the purpose of securing the assembly to the patient. Again, the cover sheet 80 merely serves as a protective cover for the adhesive and capacitive coupling when not in use or preliminary to its use.

It is to be understood from the foregoing that various modifications and changes may be made in the specific construction, composition and arrangement of parts of the preferred and modified forms of invention as set forth and described herein without departing from the spirit and scope thereof as defined by the appended claims.

We claim:

1. A dispersive electrode adapted for use with electrosurgical equipment in establishing a capacitive coupling with the skin of a mammal comprising:
    an insulated backing member;
    a substrate in the form of a flexible electrically conductive layer having one surface applied to one surface of said backing member and a second surface adapted to be applied to the skin;
    means for applying said second surface to the skin so as to define a direct capacitive interface between said second surface and the skin capable of safely dispersing current flow when used with electrosurgical equipment, said means for applying including a dielectric film applied directly to said second surface of said substrate and which when applied to the skin defines said capacitive interface between said second surface of said substrate and the skin; and
    electrical connecting means for making electrical contact with said substrate.

2. A dispersive electrode according to claim 1, wherein the thickness of said dielectric film is directly proportional to the dielectric constant of the material and directly proportional to the area of said substrate for a given voltage and frequency level.

3. A dispersive electrode according to claim 1, said insulated backing member being defined at least in part by a second layer in the form of a plastic laminate coextensive with said dielectric film.

4. A dispersive electrode according to claim 1, said dielectric film overlapping the outer peripheral edges of said substrate and being secured to said insulated backing member, and an adhesive material applied to the exposed surface of said insulated backing member in outer surrounding relation to said substrate and dielectric film.

5. A dispersive electrode according to claim 1, said insulated backing member being in the form of a flexible pad of uniform thickness being of generally rectangular configuration and provided with opposed bifurcated ends.

6. A dispersive electrode according to claim 5, said substrate including an electrically conductive tab extending from one edge of said substrate intermediately between one pair of said bifurcated ends.

7. A dispersive electrode according to claim 1, said insulated backing member having a slot therein and said substrate including an electrically conductive tab projecting from said substrate through said slot in said insulated backing member to define said electrical connecting means.

8. A dispersive electrode according to claim 1, said connecting means having complementary connector halves providing opposed confronting surfaces therebetween, and mating male and female connector portions affixed to said respective confronting surfaces so as to be disposed in aligned, facing relation to one another, said connector portions being positively connected to one another in electrical contact with said substrate while being free to swivel with respect to said substrate.

9. A dispersive electrode according to claim 8, said substrate having an opening therein, said male and female connector portions being in the form of a snap-type fastener inserted through said opening in said substrate to make electrical contact therewith.

10. A dispersive electrode according to claim 8, said connector halves being joined together including means normally biasing said connector halves to an open position.

11. A dispersive electrode according to claim 10, each of said connector halves being of generally circular configuration, said insulated backing member having a slot therein and said substrate having a tab projecting from one end through said slot in said insulated backing member, said tab having an opening therein and said male and female connector portions being interconnected through said opening formed in said tab.

12. A dispersive electrode adapted to be applied as an indifferent electrode to the skin of a patient when high frequency electrical current is employed in electrosurgical procedures, comprising a backing member; a flexible, electrically conductive layer having one surface secured to said backing member and an exposed surface, means for applying said exposed surface to the skin so as to define a direct capacitive interface between said exposed surface and the skin capable of safely dispersing current flow when used with electrosurgical equipment, said means for applying including a flexible plastic laminate applied over the exposed surface opposite to the one surface of said electrically conductive layer, said plastic laminate fully covering said electrically conductive layer, at least that portion of said plastic laminate covering said exposed surface defining a thin dielectric film which when applied to the skin forms said capacitive interface directly between said electrically conductive layer and the skin of a patient without an intervening electrolytic composition therebetween and electrical connecting means for making electrical contact with said electrically conductive layer.

13. A dispersive electrode according to claim 12, said electrically conductive layer being in the form of a metallic sheet of generally rectangular configuration and including an electrically conductive tab projecting from one end of said metallic sheet to define said electrical connecting means, and said plastic laminate encapsulating said tab along with said metallic sheet with a common opening extending through said tab and plastic laminate adapted to receive an electrical connector.

14. A dispersive electrode according to claim 12, the thickness of said dielectric film being proportional to the surface area of said electrically conductive layer multiplied by the dielectric constant of said dielectric film.

15. A dispersive electrode according to claim 12, there being a second plastic laminate adhered to said one flexible plastic laminate and encapsulating said electrically conductive layer therebetween.

16. An electrosurgical dispersive electrode assembly comprising a conductive collector plate having an opening therein, and an electrical connector having complementary connector halves providing opposed confronting surfaces therebetween, each of said connector halves being flexible and of generally circular configuration and provided with substantially flat confronting surface portions, and mating male and female connector means affixed to said respective confronting surfaces so as to be disposed in aligned, facing relation to one another, said male and female connector means being in the form of snap-type fastener elements inserted through said opening in said collector plate to make electrical contact with said collector plate and being connected together in swivelled relation to said collector plate.

17. An electrosurgical dispersive electrode assembly according to claim 16, said connector halves being joined together along a common peripheral edge and including means normally biasing said connector halves to an open position.

18. In an electrosurgical dispersive electrode assembly adapted for use with electrosurgical equipment in establishing a capacitive coupling with the skin of a mammal, the improvement comprising:
   a flexible foam pad of flat generally rectangular configuration;
   a substrate in the form of a flexible, thin, electrically conductive sheet applied to one surface of said pad;
   means for applying said substrate to the skin so as to define a direct capacitive interface between said substrate and the skin capable of safely dispersing current flow when used with electrosurgical equipment, said means for applying including a dielectric film composed of a thin, flexible laminate applied directly to said substrate to define said capacitive interface between said substrate and the skin including means joining said dielectric film, substrate and pad together with said substrate sandwiched between said pad and said dielectric film, and electrical connecting means for making electrical contact with said substrate.

19. In an electrosurgical dispersive electrode assembly according to claim 18 further including a second layer of a thin flexible laminate coextensive with said dielectric film interposed between said substrate and said pad.

20. In an electrosurgical dispersive electrode assembly according to claim 19, said dielectric film overlapping the outer peripheral edges of said substrate and being secured to said second layer, and an adhesive material applied to the exposed surface of said pad in outer surrounding relation to said substrate and dielectric film.

21. In an electrical dispersive electrode assembly according to claim 18, said pad being of generally rectangular configuration and provided with opposed bifurcated ends, said substrate including an electrically conductive tab extending from one edge intermediately between one pair of bifurcated ends to define said electrical connecting means.

22. In an electrosurgical dispersive electrode assembly according to claim 21, said bifurcated ends defined by a pair of flaps at each end diverging away from opposite ends of said pad and terminating in outer free rounded end portions.

* * * * *

UNITED STATES PATENT AND TRADEMARK OFFICE
CERTIFICATE OF CORRECTION

PATENT NO. : 4,166,465
DATED : Esty, Janet M.
INVENTOR(S) : September 4, 1979

It is certified that error appears in the above—identified patent and that said Letters Patent is hereby corrected as shown below:

Column 3, line 21, cancel "grond" and substitute -- ground --.

Column 4, line 33, cancel "on" and substitute -- in --.

Column 5, line 51, after "to", insert -- 12 --.

Column 6, line 20, cancel "positions" and substitute -- portions --.

Claim 12, Column 9, line 37, after "therebetween" insert -- , --.

Signed and Sealed this

Twentieth Day of October 1981

[SEAL]

Attest:

GERALD J. MOSSINGHOFF

*Attesting Officer*   *Commissioner of Patents and Trademarks*

REEXAMINATION CERTIFICATE (365th)

United States Patent [19]

Esty et al.

[11] B1 4,166,465

[45] Certificate Issued Jul. 9, 1985

[54] ELECTROSURGICAL DISPERSIVE ELECTRODE

[75] Inventors: Janet M. Esty, Boulder; John A. Cox, Broomfield, both of Colo.

[73] Assignee: Neomed Incorporated, Boulder, Colo.

Reexamination Request:
No. 90/000,531, Mar. 19, 1984

Reexamination Certificate for:
Patent No.: 4,166,465
Issued: Sep. 4, 1975
Appl. No.: 842,463
Filed: Oct. 17, 1977

Certificate of Correction issued Oct. 20, 1981.

[51] Int. Cl.³ .................. A61B 17/39; A61N 3/06
[52] U.S. Cl. ........................ 128/303.13; 128/798; 339/253 R; 339/255 P
[58] Field of Search ............... 128/303.13, 303.14, 128/303.17, 798, 802

[56] References Cited

U.S. PATENT DOCUMENTS

| | | | |
|---|---|---|---|
| 1,662,446 | 3/1928 | Wappler | 128/798 |
| 3,699,968 | 10/1972 | Bolduc | 128/303.13 |
| 3,848,600 | 11/1974 | Patrick et al. | 128/303.13 |

FOREIGN PATENT DOCUMENTS

| | | | |
|---|---|---|---|
| 787477 | 9/1935 | France | 128/798 |

OTHER PUBLICATIONS

Mitchell, J. P., "A Handbook of Surgical Diathermy", pp. 35-36, 1966.
Dobbie, A. K., "The Electrical Aspects of Surgical Diathermy", *Biomedical Engineering*, May 1969 Issue.
*Dental Economics*, p. 66, 1969, Blech, G. M., "Clinical Electrosurgery", p. 40, 1938.
Birtcher Catalog No. 754, Sheet on "Indifferent Plate Electrode", 6/2/69.

*Primary Examiner*—Lee S. Cohen

[57] ABSTRACT

A dispersive electrode has been devised for electromedical equipment consisting of a thin sheet or layer of electrically conductive material covered on one or both sides by a flexible laminate. To facilitate attachment to the skin of a patient during electrosurgery, the laminated sheet may be secured to a resilient backing member preferably having bifurcated ends to which an adhesive is applied in order to effect a secure connection to various parts of the body and to more readily conform to the contour of different parts of the body. The pad includes a tab projecting from one end of the conductive layer which tab is preferably of rounded or somewhat circular configuration and adapted to be inserted into a snap-type connector. The connector is in turn characterized by being a normally open connector having male and female, opposed snap-type fasteners which are pressed together through an opening in the tab into snap-fitting engagement with one another to provide a firm but flexible means of electrical connection into the plate during an electrosurgical operation. In the alternative, the tab may project rearwardly through a slot in the ground pad for connection to the electrical connector either by conventional connectors or a snap-type connector as described.

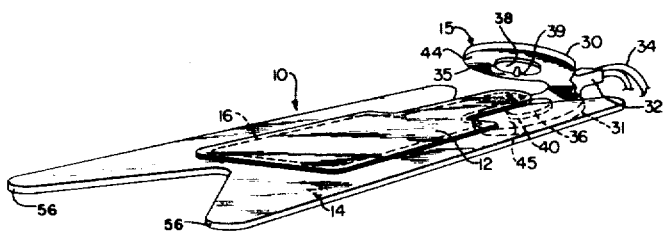

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, and 12 are determined to be patentable as amended.

Claims 2, 3, 5-11 and 13-22, dependent on an amended claim, are determined to be patentable.

1. A dispersive electrode adapted for use with electrosurgical equipment in establishing a capacitive coupling with the skin of a [mammal] *patient* comprising: [an] *a flexible* insulated backing member;
a substrate in the form of a flexible electrically conductive layer having one surface applied to one surface of said backing member and a second surface adapted to be applied to the skin;
means for applying said second surface to the skin so as to define a direct capacitive interface between said second surface and the skin capable of safely dispersing current flow when used with electrosurgical equipment, said means for applying including a *flexible* dielectric film applied directly to said second surface of said substrate and which when applied to the skin defines said capacitive interface between said second surface of said substrate and the skin, *and securing means for flexibly applying said dielectric film to the skin whereby to conform to different contours of the patient's body for the uniform dispersal of current flow therethrough*; and
electrical connecting means for making electrical contact with said substrate.

4. A dispersive electrode according to claim 1, said dielectric film overlapping the outer peripheral edges of said substrate and being secured to said insulated backing member, *and said securing means defined by* an adhesive material applied to the exposed surface of said insulated backing member in outer surrounding relation to said substrate and dielectric film.

12. A dispersive electrode adapted to be applied as an indifferent electrode to the skin of a patient when high frequency electrical current is employed in electrosurgical procedures, comprising a *flexible* backing member; a flexible, electrically conductive layer having one surface secured to said backing member and an exposed surface, means for applying said exposed surface to the skin so as to define a direct capacitive interface between said exposed surface and the skin capable of safely dispersing current flow when used with electrosurgical equipment, said means for applying including a flexible plastic laminate applied over the exposed surface opposite to the one surface of said electrically conductive layer, said plastic laminate fully covering said electrically conductive layer, at least that portion of said plastic laminate covering said exposed surface defining a thin dielectric film which when applied to the skin forms said capacitive interface between said electrically conductive layer and the skin of a patient without an intervening electrolytic composition therebetween, *including means joining said flexible plastic laminate, conductive layer and backing member together with said conductive layer sandwiched between said backing member and said flexible plastic laminate, releasable securing means for flexibly applying said dielectric film in contact with the skin whereby to conform to the contour of the patient's body for the uniform dispersal of current flow therethrough*, and electrical connecting means for making electrical contact with said electrically conductive layer.

* * * * *